United States Patent [19]

Halliday et al.

[11] Patent Number: 5,032,603
[45] Date of Patent: Jul. 16, 1991

[54] MEDICAMENTS

[75] Inventors: Clive A. Halliday, Hertfordshire; Nigel R. Oakley, Foxton, both of England

[73] Assignee: Glaxo Group Limited, England

[21] Appl. No.: 523,574

[22] Filed: May 15, 1990

[30] Foreign Application Priority Data

May 16, 1989 [GB] United Kingdom ................. 8911166

[51] Int. Cl.⁵ ............................................ A61K 31/41
[52] U.S. Cl. ................................................ 514/359
[58] Field of Search ......................................... 514/359

[56] References Cited

PUBLICATIONS

Life Sciences, vol. 33, pp. 19–29, Charney et al., Apr. 18, 1983.
Durcan et al., Psychopharmacology (1989), 97:189–193.

Primary Examiner—Stanley J. Friedman
Attorney, Agent, or Firm—Bacon & Thomas

[57] ABSTRACT

The use of the compound of formula (II) or a physiologically acceptable salt or hydrate thereof in the treatment, relief or prevention of the effects of anxiety

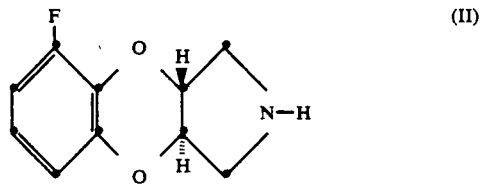

The compound of formula (II) is described in UK Published Patent Application No. 2157691A.

The preferred compound for use in this indication is (±)-trans-5-fluoro-2,3,3a,9a-tetrahydro-1H-[1,4]-benzodioxino[2,3-c]-pyrrole, especially in the form of its hydrochloride salt.

5 Claims, No Drawings

MEDICAMENTS

This invention relates to a new medical use for certain heterocyclic compounds and pharmaceutical compositions containing them. In particular it relates to the use of a benzodioxinopyrrole compound disclosed in published UK Patent Specification No. 2157691A and physiologically acceptable salts and hydrates thereof in treating anxiety.

Published UK Patent Specification No. 2157691A discloses compounds which may be represented by the formula (I)

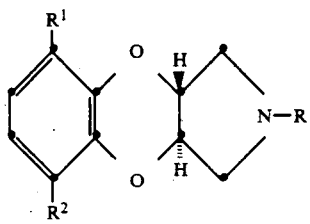

wherein R is a hydrogen atom or a group selected from $C_{1-6}$ alkyl (optionally substituted by $C_{3-7}$ cycloalkyl), $C_{3-6}$ alkenyl, $C_{3-6}$ alkynyl, $C_{3-7}$ cycloalkyl, aralkyl (in which the alkyl moiety contains 1-5 carbon atoms) and —CHO; $R^1$ is a halogen atom or a group selected from $C_{1-4}$alkyl, $C_{1-4}$alkoxy, hydroxyl, cyano, nitro and —$NR^3R^4$ where $R^3$ and $R^4$ is each a hydrogen atom or a $C_{1-4}$alkyl group; and $R^2$ is a hydrogen atom, a halogen atom or is a group as defined above for $R^1$; and the physiologically acceptable salts and hydrates thereof.

A preferred compound of formula (I), that is disclosed in GB2157691A is trans-5-fluoro-2,3,3a,9a-tetrahydro-1H-[1,4]-benzodioxino[2,3-c]-pyrrole, which may be represented by the formula (II)

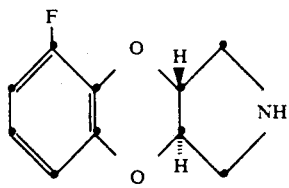

and its physiologically acceptable salts and hydrates.

The compounds disclosed in the aforementioned patent specification are described as selective $\alpha_2$-adrenoreceptor antagonists of interest in the treatment or prevention of migraine, thrombosis, diabetes, obesity, hypertension, constipation, paralytic ileus, senile dementia and in particular for the treatment of depression.

We now find that a particular compound of formula (I) is also of use in the treatment of anxiety.

Anxiety is normally treated by administering benzodiazepines such as diazepam, chlorodiazepoxide or lorazepam. However the benzodiazepines may cause a number of serious side-effects including dependence and drowsiness.

The anxiolytic activity of a particular compound of formula (I) has been demonstrated by tests in animals using, for example, the rat social interaction test, based on the experimental method described by S. File (J Neuroscience Methods, v.2. p219-238, 1980; Recent Advances in Neuropsychopharmacology, v. 31 p241-251, 1981), and the water lick conflict test, based on the experimental method described by J. R. Vogel (J. R. Vogel, B. Beer and D. E. Clody, Psychopharmacol., v.21 p1-7, 1971).

According to one aspect of the invention, we therefore provide the compound of formula (II)

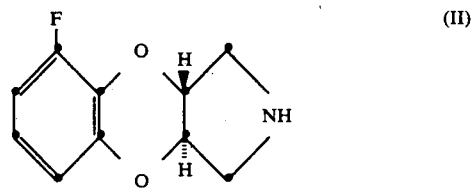

or a physiologically acceptable salt or hydrate thereof for use in treating, relieving or preventing the effects of anxiety.

In an alternative or further aspect, the invention provides a method of treatment of a mammal, including man, suffering from or susceptible to the effects of anxiety which comprises administering to a mammal in need of such treatment an effective amount of the compound of formula (II) or a physiologically acceptable salt or hydrate thereof.

It will be appreciated that whilst the compound of formula (II) will primarily be of use in the alleviation of established symptoms, prophylaxis is not excluded.

In a further aspect, the invention provides the compound of formula (II) or a physiologically acceptable salt or hydrate thereof for use in the manufacture of a medicament for treating, relieving or preventing the effects of anxiety.

Suitable physiologically acceptable salts disclosed are the acid addition salts formed with inorganic acids, for example hydrochlorides, hydrobromides, phosphates and sulphates, and with organic acids, for example citrates, tartrates, acetates, maleates and succinates.

In a particularly preferred embodiment of the present invention, the compound (of formula (II)) used is the hydrochloride, particularly in hydrated form, for example as the hemihydrate.

It will be appreciated that the compound of formula (II) is a trans isomer and exists as two enantiomers. For the avoidance of doubt, therefore, it should be noted that formula (II) depicts either isomer as well as mixtures of both somers, including racemates, even though the precise structure as set out relates only to one enantiomer.

In a particularly preferred embodiment of the present invention, the compound (of formula (II)) used is the racemate, (±)-trans-5-fluoro-2,3,3a,9a-tetrahydro-1H-[1,4]-benzodioxino-[2,3,-c]-pyrrole and its physiologically acceptable salts and hydrates, especially the hydrochloride, in particular the hydrochloride hemihydrate.

The beneficial effects of the compound of formula (II) in the treatment/relief/prevention of anxiety are particularly surprising. This is because, prior to the date of the present invention, $\alpha$-2 antagonists were thought to be anxiogenic (i.e. the cause of anxiety), rather than axiolytic. See, for example, D. S. Charney et al. Life Sciences, 1983, 33, 19, in which anxiety in humans is induced by the $\alpha$-2 antagonist, yohimbine.

The anxiolytic effect of the present compound, therefore, is unexpected and could not have been predicted from the prior art.

The compound for use according to the invention may be administered as the raw material but the active ingredient is preferably presented as a pharmaceutical formulation. The active ingredient may conveniently be presented in unit dose form.

The compound for use according to the invention may be formulated in a conventional manner using one or more pharmaceutically acceptable carriers or excipients for administration by any convenient route, for example for oral, rectal or parenteral administration. The compound for use according to the invention may be conveniently formulated for parenteral or preferably oral administration.

For oral administration the pharmaceutical composition may take the form of, for example, tablets or capsules prepared by conventional means with pharmaceutically acceptable excipients such as binding agents (for example pregelatinised maize starch, polyvinylpyrrolidone or hydroxypropyl methylcellulose); fillers (for example lactose, microcrystalline cellulose or calcium phosphate); lubricants (for example magnesium stearate, talc or silica); disintegrants (for example potato starch or sodium starch glycollate); or wetting agents (for example sodium lauryl sulphate). The tablets may be coated by methods well known in the art. Liquid preparations for oral administration may take the form of, for example, solutions, syrups or suspensions, or they may be presented as a dry product for constitution with water or other suitable vehicles before use. Such liquid preparations may be prepared by conventional means with pharmaceutically acceptable additives such as suspending agents (for example sorbitol syrup, methyl cellulose or hydrogenated edible fats); emulsifying agents (for example lecithin or acacia); non-aqueous vehicles (for example methyl or propyl-p-hydroxybenzoates or sorbic acid).

The compound for use according to the invention may be formulated for parenteral administration by injection, conveniently intravenous or subcutaneous injection, for example by bolus injection or continuous intravenous infusion. Formulations for injection may be presented in unit dosage form, for example, in ampoules or in multi-dose containers with added preservative.

The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, for example sterile pyrogen-free water, before use.

Compositions for rectal administration may be in the form of suppositories using a conventional suppository excipient.

It will be appreciated that the precise dose administered will depend on the age and condition of the patient, the particular form of the compound used, and the frequency and route of administration. The compound may be administered in single or divided doses and may be administered one or more times, for example 1 to 4 times, per day.

A proposed daily dose of the compound for administration to man for use according to the invention is 0.01 to 10 mg/kg, for example 0.05 to 3 mg/kg. The daily dose may conveniently be administered in unit dose form, each unit containing for example 0.01 to 3 mg/kg of active ingredient.

The preparation and use of a particular form of the compound of formula (II), i.e. racemic mixture of hydrochloride hemihydrate, will now be described by way of Example only.

PREPARATION ($\pm$)-trans-5-Fluoro-2,3,3a,9a-tetrahydro-1H-[1,4]-benzodioxino-[2,3-c]-pyrrole hydrochloride hemihydrate

(A) INTERMEDIATE 1

($\pm$)-(trans)-5-Fluoro-2,3-dihydro-2,3-bis[(phenylmethoxy)methyl]-1,4-benzodioxin A mixture of 3-fluorobenzene-1,2-diol (5.12 g) and (R*, R*)-($\pm$)-1,4-bis (phenylmethoxy)-2,3-butanediol, bis (4-methylbenzenesulphonate) (24.4 g) was stirred with dimethylformamide (DMF) (160 ml) under a nitrogen stream for 45 min. Anhydrous cesium carbonate (13.0 g) was added and the mixture was heated to 150° under reflux for 18 hours. The dark brown mixture was cooled to 30° and diluted with di-isopropyl ether (370 ml) and water (30 ml). The layers were separated and the aqueous layer was re-extracted with di-isopropyl ether (150 ml and then 100 ml). The extracts were sequentially washed within 1M hydrochloric acid (300 ml), 30% aqueous sodium chloride (100 ml) and were combined and evaporated in vacuo to a dark brown oil (12.6 g) which was dissolved in a light petroleum-dichloromethane (3:1) (40 ml) and chromatographed over Sorbsil (Trade Mark) (126 g) using light petroleum-dichloromethane mixtures of gradually increasing polarity. Combination of appropriate fractions and evaporation of the solvents gave the title compound as a yellow oil (7.0 g), NMR (CDCl$_3$) 2.6–2.8 (10H, m, Ph), 3.18–3.38 (3H, m, 6-H, 7-H, 8-H), 5.32–5.58 (4H, m, CH$_2$ Ph), 5.64 (2H, m, 2-H, 3-H), 6.06–6.32 (4H, m, CH$_2$O).

(B) INTERMEDIATE 2

($\pm$)-(trans)-5-Fluoro-2,3-dihydro-1,4-benzodioxin-2,3-dimethanol

Intermediate 1 (7.0 g) was dissolved in a mixture of toluene (70 ml) and anisole (7.8 ml) and the solution was stirred and cooled to $-5°$ under a gentle stream of nitrogen. Anhydrous aluminium chloride (2.4 g) was added and the temperature was maintained at 0°–5° for 20 min. More anhydrous aluminium chloride (2.4 g) was added and after 20 min. at 0°–5° the mixture was allowed to warm to 20° with continued stirring. After 20 min. at 20° it was cooled back to 0°, water (25 ml) was added and after 5 min. stirring at 20°, the mixture was diluted with ethyl acetate (75 ml) and the layers were separated. The aqueous (lower) layer was re-extracted with ethyl acetate (2×50 ml) and the organic solutions were washed with 30% aqueous sodium chloride (25 ml) and were combined and concentrated in vacuo to 36 g, giving a thick slurry of slightly purple crystals. Afte 30 min. at 20°, the crystals were harvested, washed with toluene (10 ml), light petroleum (20 ml) and diisopropyl ether (20 ml) and dried to give the title compound (2.93 g) m.p. 122°–124°. Concentration of the mother liquor gave a crude second crop of title compound (0.32 g) which after chromatographic purification afforded a further quantity of pure title compound 0.24 g, m.p. 121°–123°.

(C) INTERMEDIATE 3

(±)-(trans)-5-Fluoro-2,3-dihydro-1,4-benzodioxin-2,3-dimethanol, bis methansulphonate A solution of Intermediate 2 (3.10 g) in dichloromethane (30 ml) and triethylamine (6.4 ml) was stirred for 10 min, with ice-bath cooling. A solution of methanesulphonyl chloride (3.2 ml) in dichloromethane (10 ml) was added during 10 min. and the resultant suspension was stirred for 30 min. Water (25 ml) was added and the mixture was stirred for 20 min, the layers were then separated and the aqueous layer was re-extracted with dichloromethane (25 ml). The organic solutions were washed with water (25 ml), and were combined and evaporated to an oil which was chromatographed over Sorbsil (Trade Mark) (40 g), eluting with 9:1 dichloromethane-ethyl acetate. Appropriate fractions were combined and evaporated to a pale yellow oil (5.9 g) which crystallised slowly from ethyl acetate-disopropyl ether to afford the title compound as prisms (4.15 g) m.p. 65.5°–67.5°.

(D) INTERMEDIATE 4

(±)-(trans)-5-Fluoro-2,3,3a,9a-tetrahydro-2-(phenylmethyl)-1H-[1,4]benzodioxino[2,3-c]pyrrole A homogenised mixture of phenylmethanamine (8 ml) and Intermediate 3 (5.3 g) was heated to 130° for 15 min. then cooled to 25°. The partly crystalline mixture was partitioned between di-isopropyl ether (80 ml) and water (80 ml). The aqueous layer was re-extracted with di-isopropyl ether (100 ml) and the organic solutions were sequentially washed with 2.5% aqueous acetic acid (2 × 50 ml) amd 15% aqueous sodium chloride (100 ml) containing sodium hydrogen carbonate (5 g). They were then combined and evaporated in vacuo to an orange-brown oil (3.8 g) which crystallised spontaneously. This was recrystallised from di-isopropyl ether - light petroleum (1:1) to give pink crystals of the title compound as two crops; (1) 1.5 g m.p 79°–81° and (2) 1.4 g m.p. 79.5°–81°. Chromatography of the mother liquor gave a third crop (0.6 g)

EXAMPLE (±)-(trans)-5-Fluoro-2,3,3a,9a-tetrahydro-1H-[1,4]benzodioxino[2,3-c]pyrrole hydrochloride hemihydrate A solution of Intermediate 4 (2.3 g) in IMS (110 ml) was stirred under hydrogen at ca. 25° with 5% palladium on charcoal (1.15 g) until uptake ceased (270 ml). The catalyst was filtered off using kieselguhr pad, the filter was washed through with IMS (3 × 20 ml) and the combined filtrates were evaporated in vacuo to a pale pink oil (1.6 g). This was re-dissolved in IMS (10 ml) and 10M hydrochloric acid (1 ml) was added. After 30 min. at 20°, the resultant white crystals were harvested, washed with IMS (3 ml), 1:1 IMS -diisopropyl ether (4 ml) and di-isopropyl ether (2 × 5 ml) to afford the title compound as a hemihydrate, (1.09 g) m.p. ca. 245° (sublimes above 210°).

PHARMACOLOGICAL DATA

The anxiolyic activity of (±)-trans-5-fluoro-2,3,3a,9a-tetrahydro-1H-[1,4]-benzodioxino-[2,3-c]-pyrrole hydrochloride hemihydrate (Formula II, Racemate) was compared to a known anxiolytic, diazepam, and a known α-2 antagonist, idazoxan. The tests employed were (a) The rat social interaction test, based on the experimental method described by S File (J Neuroscience Methods, 1980, v.2, 219–238 and Recent Advances in Neuropsychopharomacology, 1981, v.31, 241-251), and (b) The water lick conflict test, based on the experimental method described by J. R. Vogel (Psychopharmacol, 1971, v.21. 1-7.)

1. THE RAT SOCIAL INTERACTION (SI) TEST

Social interaction relies on environmental manipulation to cause anxiety in rats and thus reduce the time they will spend interacting with each other. Thus, high light and unfamiliar test arena will cause control SI levels to be low and anti-anxiety agents will increase them. Lowering the light levels and using rats familiar to the test arena causes higher control levels making it easier to look for anxiogenesis which would be manifest by a fall in SI from control levels.

Pairs of age-matched, male rats are placed in the test arena, 45 mins after dosing with test compound. Social interaction (seconds) is measured via videotaped recording of behaviours, for a 10 min test period.

| | High light unfamiliar | | |
|---|---|---|---|
| Ingredient | SI (Sec) | Ingredient | SI (Sec) |
| Vehicle | 11.9 ± 3.2 | Vehicle | 13.6 ± 1.1 |
| Diazepam 1.5 | 24.6 ± 3.9* | Diazepam 1.0 | 20.9 ± 2.2* |
| Formula II, Racemate 0.05 | 18.6 ± 2.6 | Idazoxan 0.1 | 15.3 ± 2.3 |
| Formula II, Racemate 0.25 | 27.5 ± 5.6* | Idazoxan 0.5 | 15.0 ± 2.4 |
| Formula II, Racemate 1.25 | 45.3 ± 11.0** | Idazoxan 2.5 | 19.2 ± 3.2 |

Doses are as mg/kg p.o., n = 8, Results are Means ± SEM
*$p < 0.05$ **$p < 0.01$ vs vehicle

| Low light familiar | |
|---|---|
| Ingredient | SI (Sec) |
| Vehicle | 56.6 ± 10.1 |
| Diazepam 1.5 | 56.5 ± 14.4 |
| Formula II, Racemate 0.05 | 68.9 ± 15.7 |
| Formula II, Racemate 0.25 | 90.5 ± 7.5 |
| Formula II, Racemate 1.25 | 99.3 ± 10.1* |

Doses are as mg/kg p.o., n = 8, Results are Means ± SEM
*$p < 0.05$ vs vehicle.

This increase seen under those low anxiety conditions is not normally seen with other anxiolytics e.g. benzodiazepines.

2. THE WATER-LICK CONFLICT TEST

This test relies on a conflict being induced in rats, where they can either drink and accept a mild punishment (0.75 mA foot shock) or choose not to drink. To encourage them to drink they are deprived of water for 24 hr before testing. Benzodiazepines, will increase the number of shocks taken; however, some of this activity is due to a dipsogenic effect of these compounds.

| Ingredient | No. of shocks | Ingredient | No. of shocks |
|---|---|---|---|
| Vehicle | 24.6 ± 4.9 | Vehicle | 17.0 ± 4.3 |
| Diazepam 2.5 | 56.5 ± 9.5* | Diazepam 2.5 | 30.7 ± 7.3 |
| Formula II, Racemate 0.2 | 28.7 ± 5.8 | Idazoxan 0.2 | 22.3 ± 7.1 |
| Formula II, Racemate 1.0 | 43.7 ± 6.5 | Idazoxan 1.0 | 6.8 ± 1.6 |
| Formula II, | 49.2 ± 7.1* | Idazoxan 5.0 | 12.5 ± 6.7 |

| Ingredient | No. of shocks | Ingredient | No. of shocks |
|---|---|---|---|
| Racemate 5.0 | | | |

Doses are as mg/kg i.p., n = 8-16, Results are Means ± SEM
*p < 0.05 vs vehicle

FREE DRINKING

This is performed to check that the compounds picked up as positive in the water-lick conflict test do not increase water intake per se. Rats are treated as before, and the current is turned off so no shock is given. Values are therefore given as counts.

| Ingredient | No. of counts |
|---|---|
| Vehicle | 110.6 ± 6.4 |
| Diazepam 2.5 | 142.9 ± 13.3* |
| Formula II, Racemate 0.2 | 102.7 ± 10.1 |
| Formula II, Racemate 1.0 | 113.3 ± 11.0 |
| Formula II, Racemate 5.0 | 121.3 ± 8.3 |

Doses are as mg/kg i.p., n = 10, Results are Means ± SEM
*p < 0.05 vs vehicle.

The data shows that Formula II, Racemate (compound according to the invention), but not the known α-2-antagonist, idazoxan, has a positive effect in two rat models of anxiety.

We claim:

1. A method of treatment of a mammal, including man, suffering from or susceptible to the effects of anxiety which comprises administering to a mammal in need of such treatment an effective amount of the compound of formula (II) or a physiologically acceptable salt or hydrate thereof

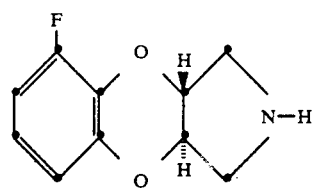

2. A method of treatment according to claim 1 which comprises administering to a mammal in need of such treatment an effective amount of (±)-trans-5-fluoro-2,3,3a,9a-tetrahydro-1H-[1,4]-benzodioxino[2,3-c]pyrrole or a physiologically acceptable salt or hydrate thereof.

3. A method of treatment according to claim 2 which comprises administering to a mammal in need of such treatment an effective amount of (±)-trans-5-fluoro-2,3,3a,9a-tetrahydro-1H-[1,4]-benzodioxino[2,3-c]pyrrole hydrochloride.

4. A method of treatment according to claim 3 which comprises administering to a mammal in need of such treatment an effective amount of (±)-trans-5-fluoro-2,3,3a,9a-tetrahydro-1H-[1,4]-benzodioxino[2,3-c]pyrrole hydrochloride hemihydrate.

5. A method of treating, relieving or preventing the effects of anxiety in a mammal, including man, which comprises administering to a mammal in need of such treatment, relief or prevention an effective amount of the compound of formula (II) or a physiologically acceptable salt or hydrate thereof.

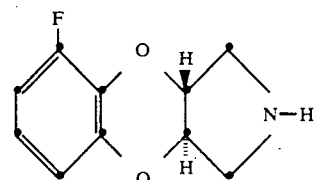

* * * * *